United States Patent [19]
Adelman et al.

[11] Patent Number: 5,482,935
[45] Date of Patent: Jan. 9, 1996

[54] ANTI-ATHEROSCLEROTIC USE OF 17 ALPHA-DIHYDROEQUILIN

[75] Inventors: Steven J. Adelman, Hatfield, Pa.; Kurt E. Steiner, Lawrenceville, N.J.

[73] Assignee: American Home Product Corporation, Madison, N.J.

[21] Appl. No.: 157,661

[22] Filed: Dec. 1, 1993

Related U.S. Application Data

[63] Continuation-in-part of Ser. No. 777, Jan. 5, 1993, abandoned.

[51] Int. Cl.[6] .................................................... A61K 31/56
[52] U.S. Cl. .......................................... 514/182; 514/824
[58] Field of Search .................................... 514/182, 824

[56] References Cited

U.S. PATENT DOCUMENTS 4,154,820  5/1979  Simoons ................................ 424/175

OTHER PUBLICATIONS

CA 111:17923, Sonnendecker et al., 1989.
Levy, R., Am. Heart J. 110: 1116 (1985).
Ross, R., New Eng. J. Med. 295:369 (1977).
Ross, R., New Eng. J. Med. 314:488 (1986).
Manderson, J. A., Arteriosclerosis 9:289 (1989).
Clowes, A. W., Circ. Res. 56:139 (1985).
Clowes, W. W., J. Cardiovas. Pharm. 14 (Suppl 6):S12 (1989).
Barrett–Connor, E., JAMA 265: (1991).
Chao, Y.–S., J. Biol. Chem. 254:11360 (1979).
Kovanen, P. T., J. Biol. Chem. 254: 11367 (1979).
Windler E. E. T., J. Biol. Chem., 255: 10464 (1980).
Stampfer, M. L., New Eng. J. Med. 313: 1044 (1985).
Utian, W. H., Obstet. Gynecol. Surv. 32: 193 (1977).
ACOG Technical Bulletin 93: 1 (1986).
Hammond, C. B., Fertil. Steril. 37:5 (1982).
Whitehead, M. I., Am. J. Obstet. Gynecol. 142:791 (1982).
Gambrell, R. D., South Med. J. 71:1280 (1978).
McDonald T. W., Am. J. Obstet. Gynecol. 127:572 (1977).
Whitehead, M. I., J. R. Soc. Med. 72:322 (1979).
Barrett–Connor, E. Annu. Rev. Med. 43:239 (1992).
Howard, et al., Arch Int. Med. 128:229 (1971).
Stern, Maturitas 4:333 (1982).

*Primary Examiner*—Kimberly R. Jordan
*Attorney, Agent, or Firm*—Richard K. Jackson

[57] ABSTRACT

A method for the treatment of atherosclerosis by administering to a patient in need of anti-atherosclerotic treatment, an effective amount of 17 alpha-dihydroequilin, a $C_2$–$C_6$ alkanoyloxy ester thereof or a pharmaceutically acceptable salt of it's sulfate or phosphate ester, in the absence of naturally occurring estrogenic sreroids. A pharmaceutical composition containing 17 alpha-dihydroequilin, a $C_2$–$C_6$ alkanoyloxy ester thereof or a pharmaceutically acceptable salt of it's sulfate or phosphate ester, in the absence of naturally occurring estrogenic sreroids, and a pharmaceutically acceptable carrier therefor.

9 Claims, No Drawings

ANTI-ATHEROSCLEROTIC USE OF 17 ALPHA-DIHYDROEQUILIN

This application is a continuation-in-part of patent application Ser. No. 08/000,777, filed Jan. 5, 1993, now abandoned.

BACKGROUND OF THE INVENTION

Cardiovascular disease (CVD) remains a leading cause of disability and death in the United States, despite great strides in its treatment over the past decades. Coronary artery disease, the major form of CVD, is the major cause of death in the United States today, responsible for over 550,000 deaths per year. Cerebrovascular disease is the third leading cause of death. The etiology of both coronary artery and cerebrovascular diseases is attributed to atherosclerosis. Through its clinical manifestations, atherosclerosis is the major cause of the more than one million heart attacks and approximately 400,000 strokes that occur each year. In addition to the high morbidity and mortality associated with atherosclerosis, it has been estimated that atherosclerosis has cost the United States' economy over $80 billion each year in lost wages, lost productivity, and medical care costs [Levy, R., Am. Heart J. 110: 1116 (1985)].

Atherosclerosis is the most important form of arteriosclerosis, involving the aorta and all of its branches. The aorta or a major artery may be involved severely with scattered and confluent atheromas in short segments next to perfectly normal vessel wall areas. The atheroma (atherosclerotic plaque) develops slowly over a period of years, finally becoming masses of lipids, mostly cholesterol and cholesterol esters. These interarterial masses reach sufficient size in the lumen of the blood vessel to obstruct blood flow, causing turbulence which may disrupt the surface of the atheroma forming a lesion and micro-emboli. Acute symptoms develop with obstruction of blood flow and as a result of the location of lodgement sites of the micro-emboli.

In the chain of events leading to atherosclerosis, it is believed that the initiating event is the formation of "fatty streaks" in carotid, coronary, and cerebral arteries, and in the aorta. These lesions are comprised of fatty deposits of cholesterol and cholesteryl ester, principally found within the smooth muscle cells and macrophages of the intimal layer [Ross, R., New Eng. J. Med. 295:369 (1977)]. Desquamation or injury of the endothelium, resulting in exposure of and possible disruption of the integrity of the extracellular matrix surrounding the cells, leads to 1) recruitment of circulating monocytes and their differentiation to macrophages, 2) accumulation of lipid in macrophages and smooth muscle cells [Ross, R., New Eng. J. Med. 314: 488 (1986)], 3) a shift in smooth muscle phenotype from a quiescent, contractile state to a migrating, proliferative form [Manderson, J. A., Arteriosclerosis 9: 289 (1989)], 4) eventual migration of transformed smooth muscle cells from the medial layer to the sub-lesion intimal layer [Clowes, A. W., Circ. Res. 56: 139 (1985)] and 5) subsequent massive proliferation of the intimal smooth muscle layer resulting in arterial luminal blockage [Clowes, A. W., J. Cardiovas. Pharm. 14 (Suppl 6): S12 (1989)].

Several risk factors have been identified in individuals who develop atherosclerosis. It can be inferred that persons with at least one risk factor will be at greater risk of developing atherosclerosis than persons with no risk factors. Persons with multiple risk factors are even more susceptible. The risk factors include hyperlipidemia (hypercholesterolemia and/or hypertriglyceridemia), hyperglycemia, diabetes, hypertension, obesity, cigarette smoking, familial hyperlipoproteinemia, aging and male sex. Peri- and postmenopausal women are one particular group of aging persons at risk for developing coronary heart disease. Since the 1950s, it has been observed that premenopausal women are protected from coronary heart disease. These observations prompted several animal studies which demonstrated that the administration of estrogens to animals fed a high fat diet prevented dietary-induced coronary atherosclerosis. [Barren-Connor, E., JAMA 265: (1991)]. One of the mechanisms by which estrogen is thought to be protective against atherosclerotic coronary heart disease is by lowering total plasma cholesterol (TPC) through induction of increased catabolism and excretion of low density lipoprotein (LDL) cholesterol into bile by the liver. This increased LDL catabolism and cholesterol excretion may be a result of an estrogen dependent increase in low density lipoprotein receptors in the liver, as has been demonstrated in rats given large pharmacologic doses of 17α-ethinyl estradiol. [Chao, Y.-S., J. Biol. Chem. 254: 11360 (1979); Kovanen, P. T., J. Biol. Chem. 254: 11367 (1979); Windler E. E. T., J. Biol. Chem., 255: 10464 (1980)]. Women who receive postmenopausal estrogen replacement therapy (ERT) have been shown to benefit from a fifty to seventy percent reduction in risk from atherosclerotic related coronary heart disease. [Stampfer, M. L., N. Engl. J. Med. 313: 1044 (1985)]. The mortality from CVD is 63% lower and the rate of mortality from myocardial infarction is between 2.3 and 2.7 times lower in estrogen-treated women compared with untreated climacteric women.

While the benefits of ERT in postmenopausal women are substantial, an association has been established between the use of unopposed ERT (estrogen therapy without concomitant progestin administration) and endometrial hyperplasia, thereby increasing the risk of endometrial carcinoma. [Utian, W. H., Obstet. Gynecol. Surv. 32: 193 (1977); ACOG Technical Bulletin 93: 1 (1986); Hammond, C. B., Fertil. Steril. 37: 5 (1982); Whitehead, M. I., Am. J. Obstet. Gynecol. 142: 791 (1982); Gambrell, R. D., South Med. J. 71: 1280 (1978); McDonald T. W., Am. J. Obstet. Gynecol. 127: 572 (1977)]. To reduce or entirely eliminate the risk of endometrial adenocarcinoma resulting from ERT while maintaining the benefits of ERT, it has been shown that progestins can be administered concomitant with the estrogen during the last 10–14 days of each estrogen cycle. [Whitehead, M. I., J.R. Soc. Med. 72: 322 (1979); Whitehead, M. I., Semin. Reprod. Endocrin. 1: 41 (1983); Barrett-Connor, E., Annu. Rev. Med. 43: 239 (1992)].

17 alpha-Dihydroequilin sulfate is approximately 15% by weight component of Premarin® conjugated estrogens (Premarin is a Registered Trademark of Wyeth-Ayerst), a drug commonly prescribed as ERT in postmenopausal women. There have been several reports of the relative estrogenicity of various estrogens to determine if they have differential effects on menopausal vasomotor symptoms, urinary gonadotropin levels, plasma lipid and lipoprotein metabolism and hepatic globulin synthesis compared to uterine response. Two studies showed that 17α -dihydroequilin had little stimulatory effect on uterine weight or maturation of vaginal cytology in the rat model and did not suppress urinary gonadotropins in postmenopausal women. Estrogenic activity was minimal. [Howard, et al., Arch Int. Med. 128: 229 (1971); Stern, Maturitas 4: 333 (1982)]. Neither study suggested the use of 17 alpha-dihydroequilin in reducing atherosclerosis.

The treatment of atherosclerosis is generally directed toward attenuation of sequelae (angina pectoris, myocardial infarction, arrhythmias, heart failure, kidney failure stroke, peripheral arterial occlusion, and related disease states) with administration of antilipidemic drugs, reduction of blood pressure by 10 to 20% and increasing high density lipid blood levels by diet and exercise. These measures are generally designed to slow the rate of progress of the disease state rather than reverse its direction.

DESCRIPTION OF THE INVENTION

In accordance with this invention, there is provided a process for treating atherosclerosis which comprises administering, orally or parenterally, an anti-atherosclerosis amount of 17 alpha-dihydroequilin as the base or in the form of a prodrug such as a $C_2$-$C_6$ alkanoyloxy ester, or a pharmaceutically acceptable salt of it's sulfate or phosphate ester. These compounds are used in accordance with this invention without any primarily estrogenic steroid present. The pharmaceutical compositions containing the anti-atherosclerotic agents of this invention in conjunction with a pharmaceutically acceptable carrier forms an additional aspect of the invention. The preferred alkanoyloxy esters are the acetoxy and pivaloyloxy esters. The preferred metal salts are the alkali metal (sodium, potassium, lithium) or alkaline earth metal (calcium or magnesium) salts. The mono-alkylamine salts contain from 1 to 6 carbon atoms, such as methylamine, ethylamine, propylamine, isopropylamine, butylamine, tertiary butylamine, hexylamine, and the like. The dialkylamine salts contain from 1 to 6 carbon atoms in each alkyl group and are produced from dimethylamine, diethylamine, diisopropylamine, di(2-methylpentyl)amine, dihexylamine, and the like.

Both arterial surface area lesions and arterial cholesterol content are reduced significantly in a dose related manner by this steroid, accompanied by a slight reduction in total plasma cholesterol. No reduction of plasma triglycerides is observed in conjunction with this use of 17 alpha-dihydroequilin. Thus, this steroid provides dramatic reduction in fatty substance deposition attending atherosclerosis, with only modest effects on plasma lipids.

The most preferred compounds, because of their water solubility, are the alkali metal salts of 17 alpha-dihydroequilin sulfate ester, including the sodium, potassium and lithium salts, which are readily absorbed in the treatment of atherosclerosis in accordance with the process of this invention when administered alone or in combination with other medicaments commonly employed in the treatment of that disease state, such as antilipidemic agents, antiarrhythmic agents, beta-blockers, and the like. The anti-atherosclerotic compounds of this invention are employed free from estrogenic steroids present in material found in natural sources of mixed estrogenic esters, such as the conjugated esters present in Premarin®. As such, they may be administered neat to a patient in need thereof, or they may be employed in conjunction with a pharmaceutically acceptable carrier. Any suitable carrier known to the an can be used to prepare the pharmaceutical compositions. In such a composition, the carrier may be a solid, liquid or mixture of a solid and a liquid. Solid compositions include powders, tablets and capsules. A solid carrier can be one or more substances which may also act as a flavoring agent, lubricant, solubilizer, suspending agent, binder, or tablet disintegrant. In powders, the carrier is a finely divided solid which is in admixture with the finely divided active ingredient. In tablets the active ingredient is mixed with a carrier having the necessary binding properties in suitable proportions and compacted in the shape and size desired. Suitable solid carriers are magnesium carbonate, magnesium stearate, talc, sugar, lactose, pectin, dextrin, starch, gelatin, tragacanth, methyl cellulose, hydroxymethyl cellulose, sodium carboxymethyl cellulose, a low melting wax, cocoa butter, and the like. Encapsulating materials may also be employed with the steroids used in the process of this invention, and the term "composition" is intended to include the active ingredient in combination with an encapsulating material as a formulation, with or without other carriers. Cachets may also be used in the delivery of the anti-atherosclerotic medicament of this invention.

Sterile liquid compositions include solutions, suspensions, emulsions, syrups and elixirs. The steroid may be dissolved or suspended in the pharmaceutically acceptable carrier, such as sterile water, sterile organic solvent or a mixture of both. Preferably the liquid carrier is one suitable for parental injection. Where the steroid is sufficiently soluble it can be dissolved directly in normal saline with or without the use of suitable organic solvents, such as propylene glycol or polyethylene glycol. If desired, dispersions of the finely divided steroid can be made-up in aqueous starch or sodium carboxymethyl cellulose solution, or in a suitable oil, such as arachis oil. Liquid pharmaceutical compositions which are sterile solutions or suspensions can be utilized by intramuscular, intraperitoneal or subcutaneous injection. In many instances a liquid composition form may be used in stead of the preferred solid oral method of administration.

It is preferred to prepare unit dosage forms of the steroid. In this way, the composition can be subdivide readily into smaller doses at the physicians direction. For example, unit dosages may be made up in packeted powders, vials or ampoules and preferably in capsule or tablet form. The active steroid present in these unit dosage forms of the composition may be present in an amount of from about 0.1 milligrams to about 2 grams or more according to the particular need of the patient. The daily dose of active steroid will vary depending upon the route of administration, the size, age and sex of the patient, the severity of the disease state, and the response to the therapy as traced by blood analysis and the patients recovery rate. By initiating the treatment regimen with a minimal dose such as 0.5 milligram, the blood levels of steroid and the patients symptomatic relief analysis may be used to determine whether a larger dose is indicated.

The treatment of atherosclerosis in men with the steroids used in this invention is favorably indicated by the fact that the 17 alpha-dihydroequilin sulfate ester salts are less estrogenic than other naturally occurring estrogens found in commercial estrogen mixtures such as Premarin®.

The 17 alpha-dihydroequilin may be obtained from natural sources such as the urine of pregnant mares and is also commercially available. The alkaline earth metal salts containing the calcium or magnesium cation are produced with the appropriate base by transmetalation of the alkali metal salt of the sulfate ester directly or via exchange with a cation exchange resin such as the weakly acidic Amberlite exchangers DP-1, IRC-50, IRC-76, CG-50 or IRP-64, on the appropriate cycle. Acidification of the alkali metal salt of the sulfate esters with a mild acid such as acetic acid, followed by extraction with an alcohol such as n-butanol and neutralization with a stoichiometric amount of calcium or magnesium hydroxide, ammonium hydroxide or the desired amine affords the other salts when desired. In the case of the amine salts, the mono-alkylamines are prepared directly from an amine, such as methylamine, ethylamine, propylamine, isopropylamine, butylamine, tertiary butylamine, hexylamine, and the like. The dialkylamine salts are produced from dimethylamine, diethylamine, diisopropylamine, di(2-methylpentyl)amine, dihexylamine, and the like. The phosphate ester salts are made in similar manner. These methods of preparation are well known in steroid chemistry and are well within the skill of the steroid chemist.

The anti-atherosclerosis properties of 17 alpha-dihydroequilin was established by testing the sodium salt of the sulfate ester in cholesterol-fed SEA quail, a subspecies of the Japanese quail, which is a standard experimental animal for investigation of aortic atherosclerosis development. In accordance with this procedure, adult, male SEA quail, approximately six months old, are caged individually with free access to food and water. The dry feed available for test and control groups of birds contains cholesterol and lard [Day, Artery 17, 49 (1989)]. The 17 alpha-dihydroequilin (75 and 15 mg) is dissolved in distilled water and mixed with 1.0 kg. of the dry feed that contains cholesterol. Actual consumption of steroid at the two feed mix levels was 5 mg/kg/day for the 75 mg/kg concentration and 1 mg/kg/day for the 15 mg/kg feed concentration. Periodic blood analysis is performed to determine total serum cholesterol concentrations, serum high density lipoprotein, and serum triglyceride concentrations. Eventually, the animals are sacrificed and the arterial surface covered with atherosclerotic lesions is directly examined to assay the area covered by the lesions. The cholesterol concentration of the artery is also determined at this time.

The results of this study demonstrated that the sodium salt of 17 alpha-dihydroequilin sulfate ester caused a slight reduction in total serum cholesterol after 8 weeks at the 5 mg/kg/day dose level (control cholesterol=2044+634 mg/dl; test animals=1469±1246 mg/dl, $p<0.05$); a slight reduction in high density lipoprotein cholesterol levels in serum after 4 weeks on the 1 mg/kg/day feed dose (control=311±93 mg/dl; test animals=250±67 mg/dl; $p<0.05$) and after 8 weeks at the 5 mg/kg/day dose level (control=301±69 mg/dl; test animals=255±65 mg/dl; $p<0.05$) and a slightly reduced serum triglyceride level at 4 weeks but not at 8 weeks of the 5 mg/kg/day dose level (control=476±197 mg/dl; test animals=362±110 mg/dl; $p<0.05$). A dramatic decrease in atherosclerotic lesions on the arterial surface of the animals fed the 5 mg/kg/day formula was observed (control=62±38 percent of total area; test animals=29±34 percent of total area; $p<0.01$). A second measure of atherosclerosis, arterial cholesterol concentration, was also dramatically decreased in the test animal group fed the 5 mg/kg/day formulation (control=30.00±12.91 mg/g; test animals=16.23±11.27 mg/g; $p<0.01$).

The anti-atherosclerosis properties of 17 alpha-dihydroequilin were also demonstrated by testing the sodium salt of the sulfate ester in cholesterol-fed ovariectomized-female New Zealand White rabbits. In accordance with this procedure, adult, ovariectomized-female rabbits are caged individually with free access to water for 24 weeks. Initially, the animals were allotted 35 g diet/kg rabbit/day. Control animals consumed only 25 g/kg/day over the first 8 weeks, thus all groups were restricted to 25 g/kg/day for the remaining 16 weeks. The dry feed available for test and control groups contains 0.2% cholesterol and 5% corn oil. The cholesterol and 17 alpha-dihydroequilin (145 mg/kg diet) is dissolved in liquid corn oil and added to the diet at so that 35 g of diet contains 5 mg of the drug. Since actual consumption of control animals was only 25 g/kg/day, the diet was restricted and actual drug consumption for the final 16 weeks was 3.58 mg/kg/day. Periodic blood analysis is performed to determine total serum cholesterol concentrations, serum high density lipoprotein, and serum triglyceride concentrations. At 24 weeks of treatment, the animals are sacrificed and the arterial surface covered with atherosclerotic lesions is directly examined to assay the area covered by the lesions. The cholesterol concentration of the artery is also determined at this time.

The results of this study demonstrated that the sodium salt of 17 alpha-dihydroequilin sulfate ester did not significantly effect plasma total cholesterol over 24 weeks of study. Total plasma cholesterols range from 833 to 993, with no significant differences between the study groups. High density lipoprotein cholesterol levels were also unaffected by drug treatment, as were triglycerides. LDL cholesterol was slightly elevated in the drug treated group, rising from 550±203 to 780±136 mg/dl ($p<0.05$). Despite the somewhat negative change in lipoprotein profile (elevation in plasma LDL cholesterol), a dramatic decrease in atherosclerotic lesions in the thoracic aorta and abdominal aorta occurred. In the thoracic aorta, 17 alpha-dihydroequilin sulfate reduced the arterial surface area covered with lesions from 26.3±27.0% in controls to 6.10±5.65% ($p<0.05$), a 77% decrease, and reduced cholesteryl ester content from 7.00±6.08 mg/g wet weight tissue to 2.08±2.39 mg/g ($p<0.05$), decreased by 70%. In the abdominal aorta, 17 alpha-dihydroequilin sulfate reduced the arterial surface area covered with lesions from 17.94±16.70% in controls to 5.14±3.47% ($p<0.05$), a 71% reduction, and reduced cholesteryl ester content from 3.82±3.05 mg/g wet weight tissue to 1.30±0.65 mg/g ($p<0.05$), decreased by 66%.

From this data it is apparent that 17 alpha-dihydroequilin itself and in the form of its 3-alkanoyloxy esters, and alkali metal, alkaline earth metal, ammonium, alkylamine and dialkylamine salts of sulfate or phosphate esters, is a very effective agent useful in the direct reduction of arterial lesions attending the progression of atherosclerosis. Hence, this invention provides a direct method for alleviating what is probably the most severe symptom of that disease state without markedly changing other blood chemistry.

What is claimed is:

1. A method for the treatment of atherosclerosis which comprises administering to a patient in need of anti-atherosclerotic treatment, an effective amount of 17 alpha-dihydroequilin, a $C_2$–$C_6$ alkanoyloxy ester thereof or a pharmaceutically acceptable salt of it's sulfate or phosphate ester, in the absence of naturally occurring estrogenic steroids.

2. The method of claim 1 in which said pharmaceutically acceptable salt is the sodium salt.

3. The method of claim 1 in which said pharmaceutically acceptable salt is the potassium salt.

4. The method of claim 1 in which said pharmaceutically acceptable salt is the lithium salt.

5. The method of claim 1 in which said pharmaceutically acceptable salt is the calcium salt.

6. The method of claim 1 in which said pharmaceutically acceptable salt is the magnesium salt.

7. The method of claim 1 in which said pharmaceutically acceptable salt is the ammonium salt.

8. The method of claim 1 in which said pharmaceutically acceptable salt is the diethylamine salt.

9. A method for removing arterial lesions attending the development of atherosclerosis which comprises administering, orally or parenterally, to a patient suffering from atherosclerosis, a pharmaceutical composition containing an anti-atherosclerotic amount of an alkali metal salt of 17 alpha-dihydroequilin.

* * * * *